(12) United States Patent
Buglino et al.

(10) Patent No.: US 7,947,025 B2
(45) Date of Patent: May 24, 2011

(54) POUCH FOR COLLECTING HUMAN BODY WASTE AND DRAINAGE ADAPTER THEREFOR

(75) Inventors: Donald E. Buglino, Titusville, NJ (US); Matt Dawson, Hillsborough, NJ (US); Bret Weig, Browns Mills, NJ (US); Adrian Breakwell, Cheshire (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 892 days.

(21) Appl. No.: 11/462,085

(22) Filed: Aug. 3, 2006

(65) Prior Publication Data

US 2009/0082743 A1    Mar. 26, 2009

Related U.S. Application Data

(60) Provisional application No. 60/705,688, filed on Aug. 4, 2005.

(51) Int. Cl.
*A61F 5/44* (2006.01)
(52) U.S. Cl. ......... 604/335; 604/332; 604/334; 604/340
(58) Field of Classification Search .................... 604/335
See application file for complete search history.

(56) References Cited

U.S. PATENT DOCUMENTS

| 3,825,005 | A | * | 7/1974 | Fenton | 604/335 |
| 3,841,332 | A | * | 10/1974 | Treacle | 604/335 |
| 4,084,590 | A | * | 4/1978 | Caraway et al. | 604/335 |
| 5,364,378 | A | * | 11/1994 | Denard | 604/335 |
| 5,792,127 | A | | 8/1998 | Marran | |
| 6,280,431 | B1 | * | 8/2001 | Domkowski et al. | 604/411 |
| 6,419,664 | B1 | | 7/2002 | von Bulow et al. | |
| 6,635,036 | B1 | | 10/2003 | Tanghoej et al. | |
| 6,849,066 | B1 | * | 2/2005 | Ciok et al. | 604/332 |
| 2004/0049837 | A1 | | 3/2004 | Falconer et al. | |

FOREIGN PATENT DOCUMENTS

DK    WO03/086249    10/2003
EP    1 378 218 A1 *    1/2004

* cited by examiner

*Primary Examiner* — Melanie J Hand
*Assistant Examiner* — Ginger T Chapman
(74) *Attorney, Agent, or Firm* — Stuart E. Krieger

(57) ABSTRACT

A drainable urine pouch includes a discharge portion that is foldable between a discharge position and a closed position. A security flap is sealed to both walls of the pouch by a through weld, to define a baffle near the discharge portion. The discharge portion includes a constriction, and a stepped profile with multiple step stages. The discharge portion has one or more bias members. A drainage adapter is releasably coupled to the discharge portion. The drainage adapter has a plug with a shoulder for abutting the constriction in the discharge portion, to locate the adapter correctly for obtaining a liquid-tight seal.

9 Claims, 14 Drawing Sheets

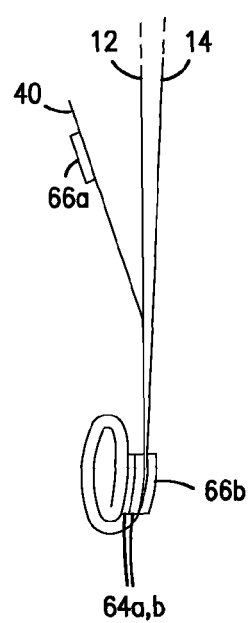 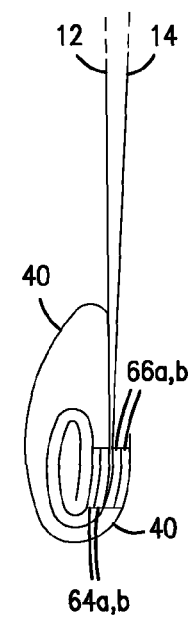
FIG. 5A  FIG. 5B

POUCH FOR COLLECTING HUMAN BODY WASTE AND DRAINAGE ADAPTER THEREFOR

FIELD OF THE INVENTION

The present invention relates to the field of collection pouches for human body waste and, in particular, to a drainable collection pouch. The pouch is intended to collect liquid. For example, the pouch may be a urostomy pouch or a urine collection pouch. The invention also relates to a drainage adapter for a pouch.

BACKGROUND TO THE INVENTION

A common type of drainable urostomy pouch comprises a drainage tap or valve arrangement at its lower end, through which collected urine may be emptied. However, the tap or valve arrangement represents significant additional manufacturing inconvenience and cost, making the pouch more expensive to produce. The tap or valve components have to be molded separately from the pouch, and then fastened to the pouch. Often, a tap comprises plural components that cannot be pre-assembled, requiring assembly to be completed after attachment to the pouch. The integrity of the pouch depends on the tap or valve arrangement, and it is often not possible to quality-test a tap or valve prior to installation on the pouch.

U.S. Pat. No. 6,419,664 describes a drainable urostomy pouch comprising an elongated discharge portion provided by an extension of the pouch walls. The discharge portion is foldable into a closed condition which is said to seal the discharge portion. The discharge portion has a relatively narrow internal drain passage, the width of which is less than 60% of the external width of the discharge portion. The drain passage has a generally fluted shape tapering smoothly to a narrow portion within the discharge portion. When the discharge portion is folded to its closed condition, the drain passage is collapsed to seal the discharge portion. However, the drain passage is narrow, and may stick in its collapsed state (so-called pancaking) when the discharge portion is unfolded. U.S. Pat. No. 6,419,664 teaches permanently sealing a tube in the discharge portion to expand the drain passage when the discharge portion is unfolded. However, such a tube inevitably obstructs tight folding of the discharge portion when in its closed condition, possibly reducing the integrity of the seal and creating excessive bulging when a compact folded shape would be far more desirable to the wearer.

U.S. Publication No. 2004-0049837-A1 discloses a more refined drainable urostomy pouch also comprising a foldable elongated discharge portion formed as an extension of the pouch walls. Deformable bias strips provided at the distal end of the discharge portion enable the degree of distention of the discharge outlet to be manually controlled by the user, to thereby control the rate of flow of the liquid contents during emptying. The content of U.S. Publication No. 2004-0049837-A1 is incorporated herein by reference.

SUMMARY OF THE INVENTION

Broadly speaking, a first aspect of the invention provides a drainable pouch for collecting human body waste, comprising first and second walls defining a collection region and a discharge portion depending from the collection region, the discharge portion being configured to be foldable to a closed position in which the discharge portion is sealed closed.

The pouch may be a liquid collection pouch and/or an ostomy pouch.

The discharge portion includes a discharge passage defined only by portions of the first and second walls. The discharge portion may be absent an additional tube member permanently sealed within the discharge portion.

The first aspect additionally includes one or more of the following preferred features:

(A) The pouch further comprises a flap foldable to at least partly embrace the discharge portion when in the closed position.

The flap is permanently sealed to both the first and second walls by a seal extending through at least one of the first and second walls to the other. The seal is a through-weld. The seal is near or at the discharge portion.

Attaching a flap using such a seal simplifies manufacture compared to attaching a flap to just one wall without also involving the other wall in the attachment process. Moreover, the seal provides an advantageous baffle effect within the pouch.

(B) The pouch further comprises a baffle located adjacent to the discharge portion. The baffle is formed by a direct seal between the first and second pouch walls. As explained above, the baffle may optionally be provided by a seal associated with a flap.

The baffle is configured as an island not intersecting a side seal of the pouch. Clearances exist around either end of the baffle. The baffle is effective in controlling bulging of the pouch when the pouch is full of liquid. Additionally or alternatively, the baffle is effective in controlling at least partly a rate of discharge of the liquid through the discharge portion when the pouch is being drained.

(C) The discharge portion comprises a drain passage having a constricted region. Optionally, at least a portion of the drain passage downstream of the constricted region has an internal width greater than the internal width in the constricted region. The discharge opening of the discharge portion has a width wider than the internal width in the constricted region.

The constricted region functions to control the rate of flow of liquid through the drain passage when the pouch is being drained.

Additionally or alternatively, the constricted region functions as a stop for locating a portion of a drainage adapter insertable into the discharge opening. The stop aids easy positioning of the drainage adapter inside the discharge portion, in a correct position for achieving a liquid-tight seal.

Additionally or alternatively, the constricted region functions as a region against which a drainage adapter insertable into the discharge opening, forms a seal, in use.

(D) The pouch further comprises a stepped region between a relatively wide collection region of the pouch, and the discharge portion. The stepped region includes multiple step stages. The stepped region includes a first step stage narrowing the width of the pouch to an intermediate width, and a second step stage narrowing the intermediate width to the width of the discharge portion.

The steps in the pouch width may be steps in the internal width and/or the external width.

The stepped portion is highly effective in controlling the shape of the pouch when containing collected matter. The stepped portion is especially advantageous in combination with a baffle at or near the stepped region.

(E) The pouch further comprises at least one bias member located at the discharge portion. Additionally or alternatively, the pouch further comprises a permanent island seal between the first and second walls, the island seal not intersecting a side seal of the pouch.

A second aspect of the invention generally provides a drainage adapter in isolation, or in combination with a drainable, human body waste collection pouch. The drainage adapter is couplable to the discharge portion of the pouch for draining the contents to another location. The pouch may include any of the features of the first aspect.

The drainage adapter includes one or more of the following features:

(A) The drainage adapter includes first and second portions for insertion into the discharge opening of the pouch. The second portion is wider than the first portion. The second portion defines a shoulder with respect to the first portion. The shoulder is configured to abut a constriction inside the discharge portion of the pouch, for aiding proper positioning of the adapter. This is especially effective in enabling the adapter to be positioned optimally without the user needing to view inside the discharge portion.

The first portion and/or the second portion has a shape that is generally oval, or generally eye-shaped, or generally almond-shaped. Such a shape achieves an optimum fit within the discharge portion, especially when the discharge passage is defined only by the first and second walls, and not by an additional tube member permanently sealed inside the discharge portion of the pouch.

(B) The drainage adapter comprises a plug, an actuator, and a controller for the actuator. The actuator is configured for selectively enlarging and/or reducing a size of a distal end of the plug. The controller is located at a proximal end of the plug, to enable easy operation by a user from outside the pouch, even when the plug is inserted in the discharge opening.

(C) The drainage adapter comprises a plug and a clamp. The plug is insertable into the discharge portion of the pouch. The clamp is operable to clamp the material of the discharge portion around the plug, to form a liquid-tight seal against the plug.

Various forms of clamp are envisaged. The clamp may be a separate member from the plug, or it may be coupled to the plug. The plug may further comprise supports for supporting the clamp limbs relative to the plug. In one form, the clamp hinges open about a hinge axis generally parallel to an axis of the plug. In another form, the clamp hinges open about an axis generally perpendicular to an axis of the plug.

The above aspects and/or features may be used independently of each other, or additional advantages may be obtained by using two or more in combination. The combination of drainable pouch and adapter may also be referred to as a drainable collection system.

Further features and advantages of the invention are described in the claims and the following description. Protection is claimed for any novel feature and/or combination of features described herein and/or illustrated in the drawings, whether or not emphasis has been placed thereon.

BRIEF DESCRIPTION OF THE DRAWINGS

FIG. 5a is a schematic side view showing the discharge portion in its closed condition.
FIG. 5b is schematic side view showing the discharge portion in its closed condition.

DETAILED DESCRIPTION OF THE INVENTION

Figure 1:
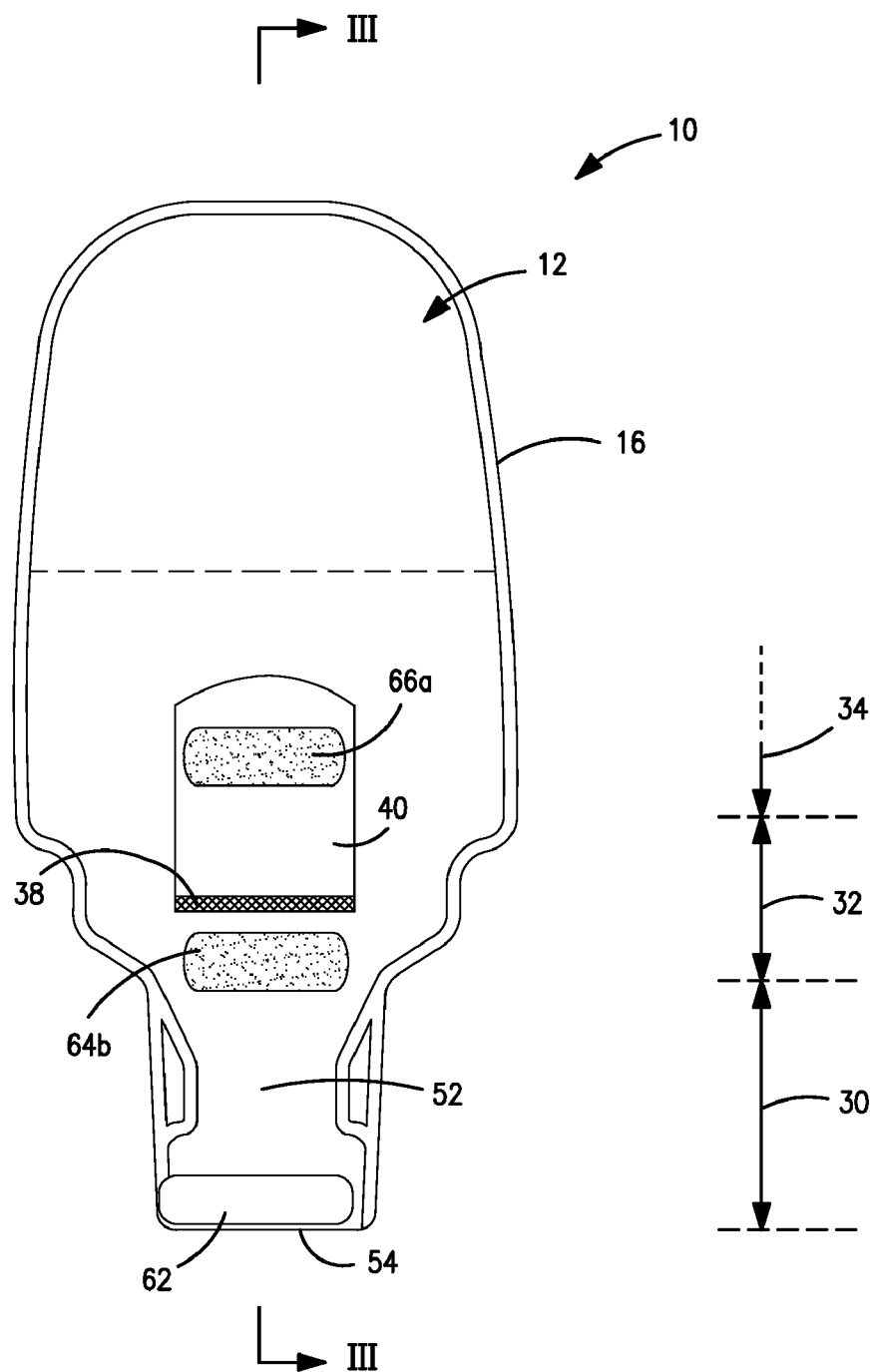
FIG. 1 is a schematic front view of a urostomy pouch.
Figure 2:
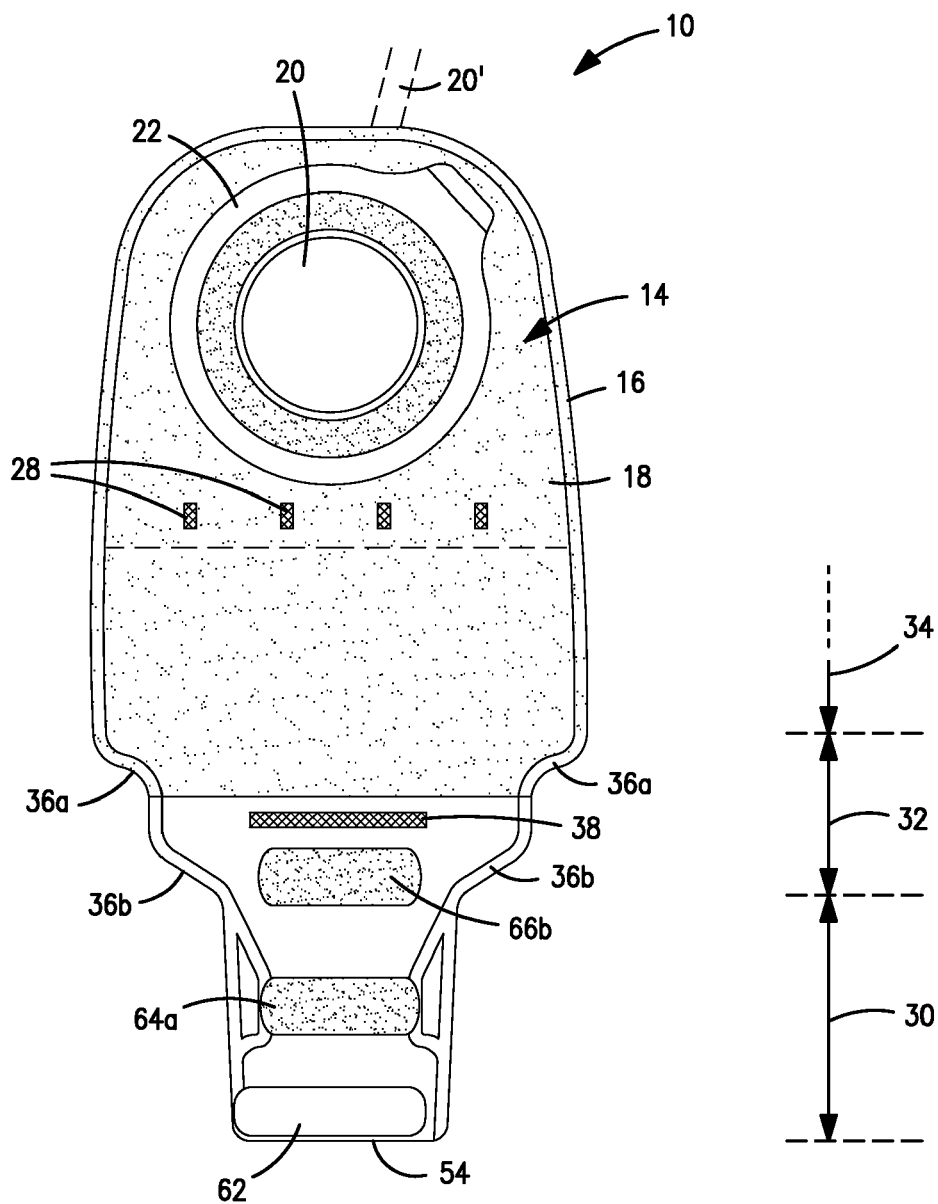
FIG. 2 is a schematic rear view of the pouch of FIG. 1.

Referring to FIGS. 1-5, a pouch 10 for collecting liquid human body waste is illustrated. The pouch 10 may, for example, be a urostomy pouch or a urine collection pouch (e.g., for incontinent persons).

The pouch 10 generally comprises a front wall 12 and a rear wall 14 of flexible plastics film generally impermeable to liquid. The front wall 12 and the rear wall 14 are secured together around a peripheral seam 16. The seam 16 may be a welded or heat-sealed seam 16. A so-called comfort layer 18 of a relatively soft material is provided on the exterior of one, or both, of the front and rear walls 12 and 14. In the present embodiment, the comfort layer 18 is provided on at least the wall facing towards the body, e.g., the rear wall 14.

An entrance aperture 20 is provided in an upper region of the pouch 10. The illustrated embodiment is a urostomy pouch, and the entrance aperture (e.g., a stomal aperture) 20 is provided in the rear wall 14. An attachment device 22 is provided around the entrance aperture 20 for directly or indirectly attaching the pouch 10 when worn on the body. For example, the attachment device 22 comprises a plate or wafer of skin-compatible adhesive for directly attaching the pouch to the wearer's skin. Alternatively, the attachment device 22 comprises part of a separable fastener for releasably fastening the pouch 10 to a mounting wafer (not shown) worn on the body. The fastener may be an adhesive-based fastener, or a mechanical engagement faster. In an alternative form of collection pouch 10 (e.g., for an incontinence collection pouch), the entrance aperture comprises an inlet tube (shown in phantom at 20') entering an upper region of the pouch 10 instead of the stomal aperture 20 in the rear wall 14.

Figure 3:
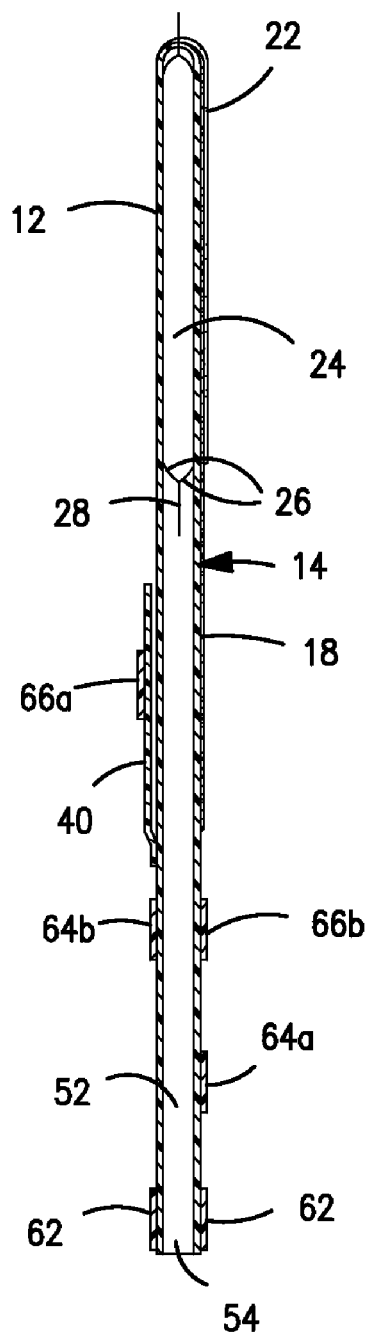
FIG. 3 is a schematic section along the line III-III of FIG. 1.
Figure 4:
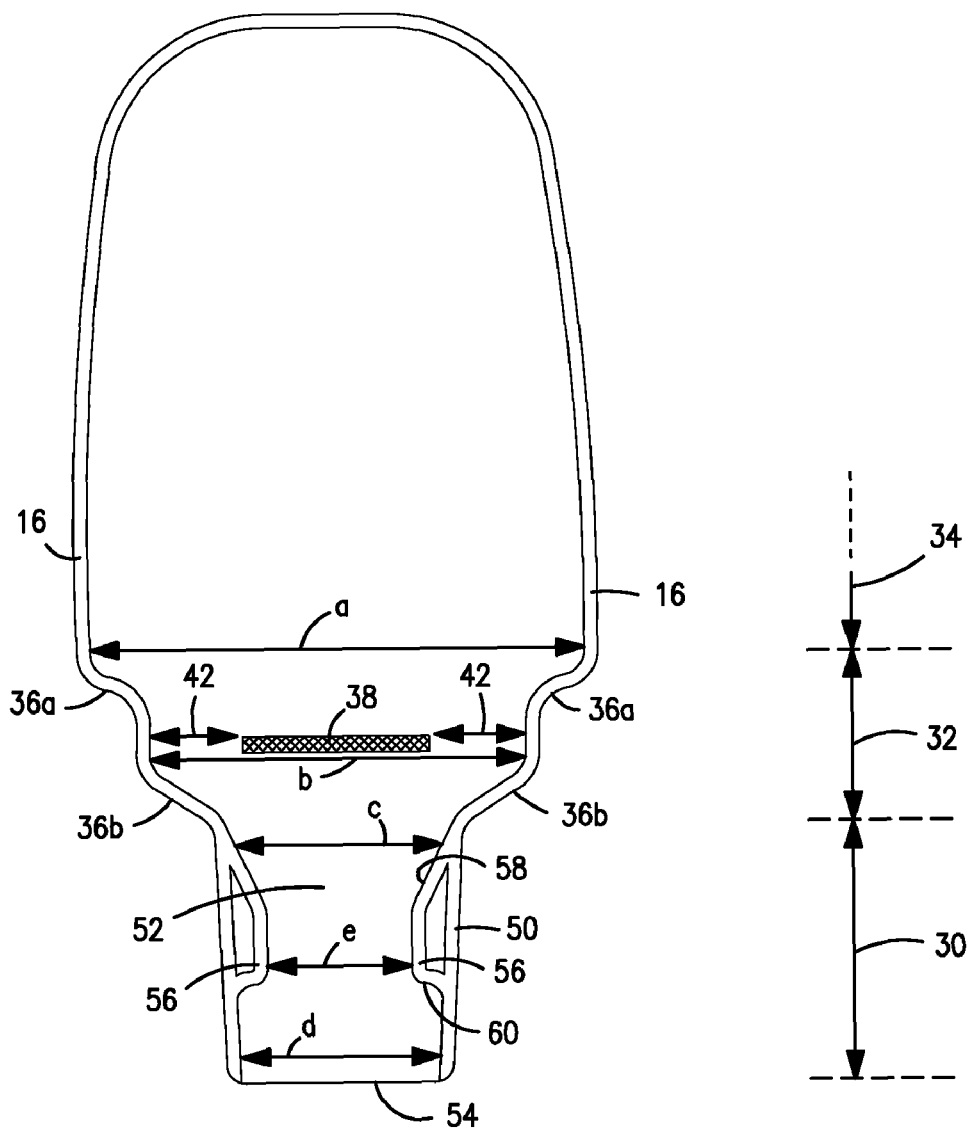
FIG. 4 is a schematic interior view showing the interior volume of the pouch of FIG. 1.
Figure 6:
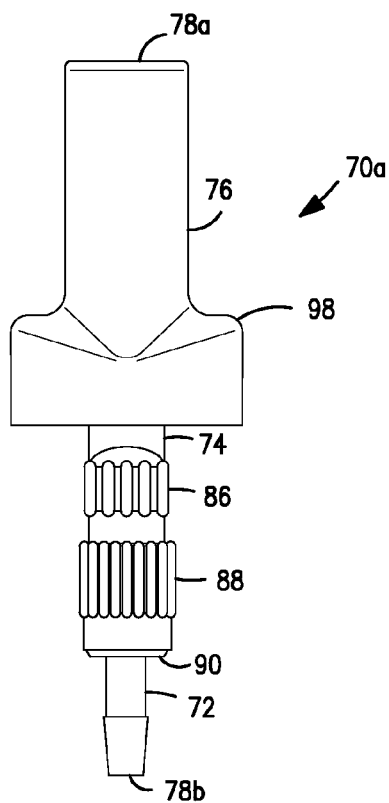
FIG. 6 is a side view of a first example of drainage adapter.

The pouch 10 includes an anti-sloshing or non-return valve 24, for obstructing liquid collected within the pouch 10 from splashing back to the entrance aperture 20 (or 20') as the wearer moves around. The non-return valve 24 comprises one or more curtain sheets 26 joined to each other and/or to the front wall 12 and/or to the rear wall 14 at spaced apart positions 28, to define a flap valve. The present embodiment includes two curtain sheets 26 suspended between the front and rear walls 12 and 14, to define a suspended flap valve (as shown in FIG. 3).

The lower region of the pouch 10 generally comprises a discharge portion 30, and a stepped portion 32 at the proximal (or upper) end of the discharge portion 30. The discharge portion 30 and/or the stepped portion 32 are formed by extensions of the front and rear walls 12 and 14, to be integral with the remainder of the pouch 10.

The stepped portion 32 generally comprises at least one step-down profile from a relatively wide portion 34 of the pouch 10 (e.g., a main collecting region of the pouch), and a relatively narrower width of the discharge portion 30. In the illustrated embodiment, the stepped portion 32 includes plural, e.g. first and second, distinct step stages 36a and 36b. One or more of the step stages may have a relatively abrupt step shape (e.g., the step 36a) and/or one or more of the step stages may have a relatively gradually tapered shape (e.g., the step 36b). The multiple step stages of the stepped portion define a multiple-S profile (e.g., a double-S profile in the illustrated embodiment). The stepped portion 32 may be symmetrical on the left and right sides of the pouch 10, or it may be asymmetrical. The first step stage 36a reduces the width from a first distinct width "a" to a second distinct width "b". The second step stage 36b reduces the width from the second distinct width to a third distinct width "c". The term "distinct width" refers to a width that is relatively stable or identifiable compared to an adjacent region in which the width may change significantly.

References herein to a "width" refers to the width when the pouch is in a generally flat and/or empty condition.

A baffle 38 is formed between the front and rear walls 12 and 14. The baffle 38 is formed in the stepped portion 32. In the present embodiment, the baffle 38 provides an island seal directly between the front and rear walls 12 and 14. The island seal may be a weld. The baffle 38 is provided by a through weld attaching a flap 40 (described in more detail below). Alternatively, the baffle 38 comprises a wall or pleat between the front and rear walls 12 and 14. The baffle 38 joins the front and rear walls 12 and 14.

A clearance 42 exists to one or both sides of the baffle 38. The baffle 38 is generally straight (as illustrated), or it may be curved. The baffle 38 is continuous (as illustrated), or it may be discontinuous (for example, formed by spaced apart baffle segments, such as spot welds). The baffle is formed to be generally aligned (e.g., in a vertical direction) with either one of the steps 36a and 36b of the stepped portion, or with a middle position between steps 36a and 36b. The lateral dimension of the baffle 38 is less than about 80% of the internal width of the pouch 10 in the region around the baffle 38 (for example, the width "b" in the illustrated embodiment). The lateral dimension is less then about 70%, or less then about 60%, for example, about 50%, of the internal width. The lateral dimension is at least about 30%, or at least about 40% of the internal width.

The baffle 38 provides one or more of the following characteristics:

(a) The baffle 38 helps control bulging of the pouch 10 when the pouch is full of collected liquid. The configuration of the stepped region 32 additionally helps control the shape of the pouch 10. In particular, the configuration of the stepped region 32 helps avoid a tendency of the pouch 10 to fold around the baffle 38 when the pouch 10 is full, which might otherwise completely constrict the clearances 42 and make drainage difficult.

(b) The baffle 38 helps to control the rate at which the liquid contents drain through the discharge portion 30, and, in particular, avoids a sudden discharge when the discharge portion 30 is opened.

(c) In the illustrated form, the baffle 38 is through weld formed when the flap 40 is attached to the pouch. Forming a through weld simplifies the manufacturing process by enabling a welding process involving both of the pouch walls. Forming a through weld is simpler than welding the flap 40 selectively to only one pouch wall without involving the other pouch wall.

The discharge portion 30 comprises sealed side edges 50 defining a drain passage 52 therebetween. The drain passage 52 communicates with a discharge opening 54 at the distal or lower end of the discharge portion 30. The sealed side edges 50 are integral with and/or a continuation of the seam 16. A lateral constriction 56 is formed in the drain passage 52 upstream of the discharge opening 54. The constriction 56 constricts the lateral width of the drainage passage 52. The constriction 56 controls the rate at which liquid drains through the drain passage 52 (as an alternative to, or in combination with, the baffle 38). The constriction 56 terminates before the discharge opening 54, such that a width "d" of the drain passage 52 at the outlet 54 is greater than a width "e" of the drain passage 52 (e.g., the minimum width) in the region of the constriction 56. The constriction 56 is defined by portions or extensions of the seam 16 at the side edges 50 of the discharge portion 30. The constriction 56 has a relatively gradual ramp profile 58 at its upwardly facing region, and a relatively abrupt profile 60 facing towards the discharge opening 54. The relatively gentle ramp portion 58 provides for smooth liquid flow during emptying of the pouch. The relatively abrupt profile 60 provides an anti-drip feature. The constriction 56 (and in particular the lower profile 60) additionally, or alternatively, provides a stop for accurately locating a plug portion of an adapter insertable into the discharge portion (as described later below).

One or more bias members 62 are provided at the discharge opening 54. The, or each, bias member may be of plastics and may be capable of flexing. In the present embodiment, two bias members 62 are used, one on each of the front and rear walls 12 and 14. However, in an alternative embodiment, a single bias member may be used on only one wall, as desired. Each bias member 62 functions to bias the shape of the discharge opening 54. Each bias member 62 is normally flat, or near flat, to bias the opening 54 closed or nearly closed. The bias member(s) 62 are resiliently deformable upon application of finger pressure to the opposite ends of the bias member(s) 62 to distend the discharge opening 54. Alternatively, each bias member 62 is shaped to hold the opening 54 at least partway open in the relaxed state of the bias member 62. The bias member(s) 62 are resiliently deformable to allow the opening 54 to be closed by flattening the bias member(s) 62, for example, against each other if two bias members 62 are used. Two bias members 62 are offset laterally with respect to each other, which has been found to promote bending of the bias members 62 in opposite directions, as desired. Further constructional details of the bias members 62 are found in the aforementioned U.S. Publication No. 2004-0049837-A1. The discharge portion 30 is configured to be closed by rolling or folding the discharge portion 30 one or more times, in a direction towards the main collecting region of the pouch 10 (as shown in FIGS. 5a and 5b). The bias member(s) 62 define a unit fold length around which the discharge portion 30 is folded. A discharge portion fastener 64 is provided by mateable parts 64a and 64b of a distributed mechanical engagement faster. The mateable parts 64a and 64b are located on the front and rear faces of the pouch 12 in relative positions such that the parts 64a and 64b come into face-to-face registration when the discharge portion 30 is folded to a fully closed position.

The aforementioned flap 40 is provided as additional security for preventing accidental release of the discharge portion fastener 64. As best seen in FIG. 5b, the flap 40 is configured to be foldable around or under the folded discharge portion 30, as a shield. A flap fastener 66 is provided by mateable parts 66a and 66b of a distributed mechanical engagement fastener carried on the flap 40 and an opposite face of the pouch 10, for securing the flap 40 when folded around the discharge portion 30. In the present embodiment, the flap 40 is provided on the front wall 12 of the pouch, and the flap fastener part 66b is provided on the rear wall 14, although the relative positions may be reversed as desired.

The distributed mechanical engagement fasteners 64 and 66 may, for example, be of hook and loop material. However, it may be preferred to use a hook-hook (or "male-male") type fastener instead. Such a fastener enables all of the fastener parts 64a, 64b, 66a and 66b to be plastics extrusions, which may enable the ostomate to more easily wash and/or dry the fastener parts.

Further details of the folding and opening of the discharge portion 30, the use of the flap 40, and the configuration of the fasteners 64 and 66 are found in the aforementioned U.S. Publication No. 2004-0049837-A1.

It will be appreciated that the invention, particularly as illustrated in the preferred embodiment, enables a liquid collection pouch 10 to be provided without any tube member embedded permanently in discharge portion. The absence of a tube member enables the discharge portion 30 to be folded tightly into its closed position to achieve both a tight seal, and a compact shape avoiding significant undesirable bulging.

FIGS. 6-18 illustrate embodiments of adapters 70a, 70b, 70c and 70d connectable to the discharge portion 30, to enable the contents of the pouch to drain into a remote collector (not shown). Such adapters 70 are useful for continuous drainage of the pouch 10, for example, while the user is sleeping. The adapters 70 are especially configured to form a reliable liquid-tight seal to the discharge portion 30 even in the absence of a round tube embedded in the discharge portion 30.

Referring to FIGS. 6-11, a first example adapter 70a is illustrated. The adapter 70a is intended for at least partial insertion into the outlet portion 30. The adapter 70a includes a self-anchoring configuration for anchoring the adapter internally with respect to the constriction 56 of the discharge portion 30. The self-anchoring configuration comprises a device that is insertable into or through the constriction 56, and is expandable at or behind the constriction 56 to anchor the device within, or from one or both sides of, the constriction 56.

The adapter 70a generally comprises a central tube 72, an enlargement actuator 74, and an expandable cover 76. The central tube 72 is hollow and be open at opposite ends 78a and 78b for fluid flow through the central tube 72. The expandable cover 76 is integrally formed (e.g., integrally molded) with the central tube 72, or bonded thereto, to define a unitary item. The expandable cover 76 is sealed to the central tube 72 at the distal end 78a, and define an annular clearance 80 (e.g., an annular well) that is open from below, between the outer cover 76 and the central tube 72. The enlargement actuator 74 is carried on the central tube, and extend into the annular clearance 80. The enlargement actuator 74 comprises expansion tongues 82 that is arranged to be driven outwardly by actuator cams (not shown) upon relative displacement between the enlargement actuator 74 and the central tube 72.

The displacement is axial displacement and/or rotary displacement, as desired. When displaced outwardly, the tongues 82 impart an enlarged bulged head to the expandable cover 76, as depicted in phantom at 84 in FIGS. 8 and 11. The exact shape of the bulged end 84 varies depending on the configuration of the outer cover 76, and the material from which the outer cover 76 is made. The outer cover 76 may be of any suitable material, for example, an elastomer. The lower end of the enlargement actuator 74 opposite the tongues 82 is formed with a finger grippable surface 86, for example, a splined surface.

Figure 7:
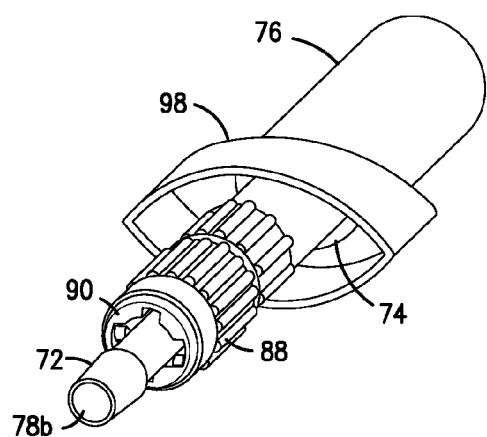
FIG. 7 is a perspective view from below of the drainage adapter of FIG. 6.
Figure 8:
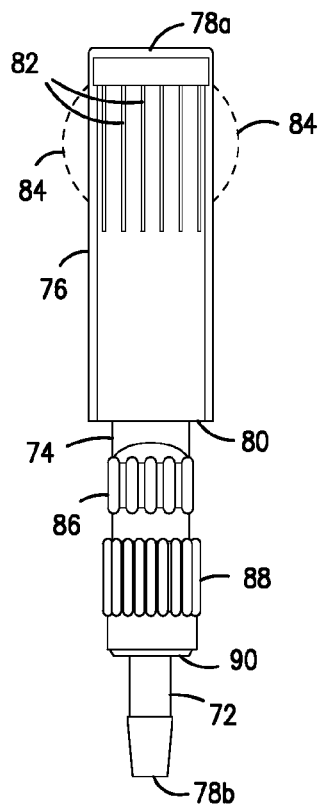
FIG. 8 is a partial cutaway view from another side of the drainage adapter of FIG. 6.
Figure 9:
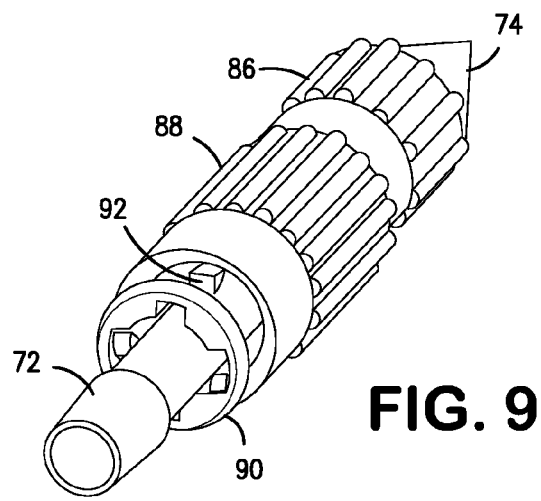
FIG. 9 is a perspective view showing a detail of the drainage adapter.
Figure 10:
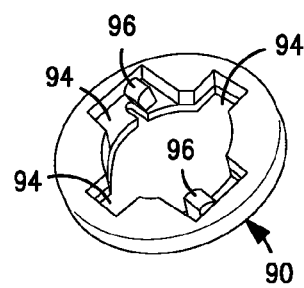
FIG. 10 is a perspective view showing a retainer ring of the drainage adapter in isolation.

The enlargement actuator 74 is retained captive on the central tube 72 by a counter-grip 88 and/or a retaining ring 90. The counter-grip 88 has a finger grippable surface similar to the enlargement actuator 74. The retaining ring 90 is securable to the central tube 72 by a bayonet-style engagement between studs 92 on the central tube 72 and receiving recesses 94 in the retaining ring 90. The receiving recesses 94 includes cantilever snaps 96 for trapping the studs 92 in a fully engaged condition in the recesses 94 (as best seen in FIGS. 7 and 9). Alternatively, if the retaining ring 90 is omitted, the counter-grip 88 may be bonded directly to the central tube 72.

Figure 11:
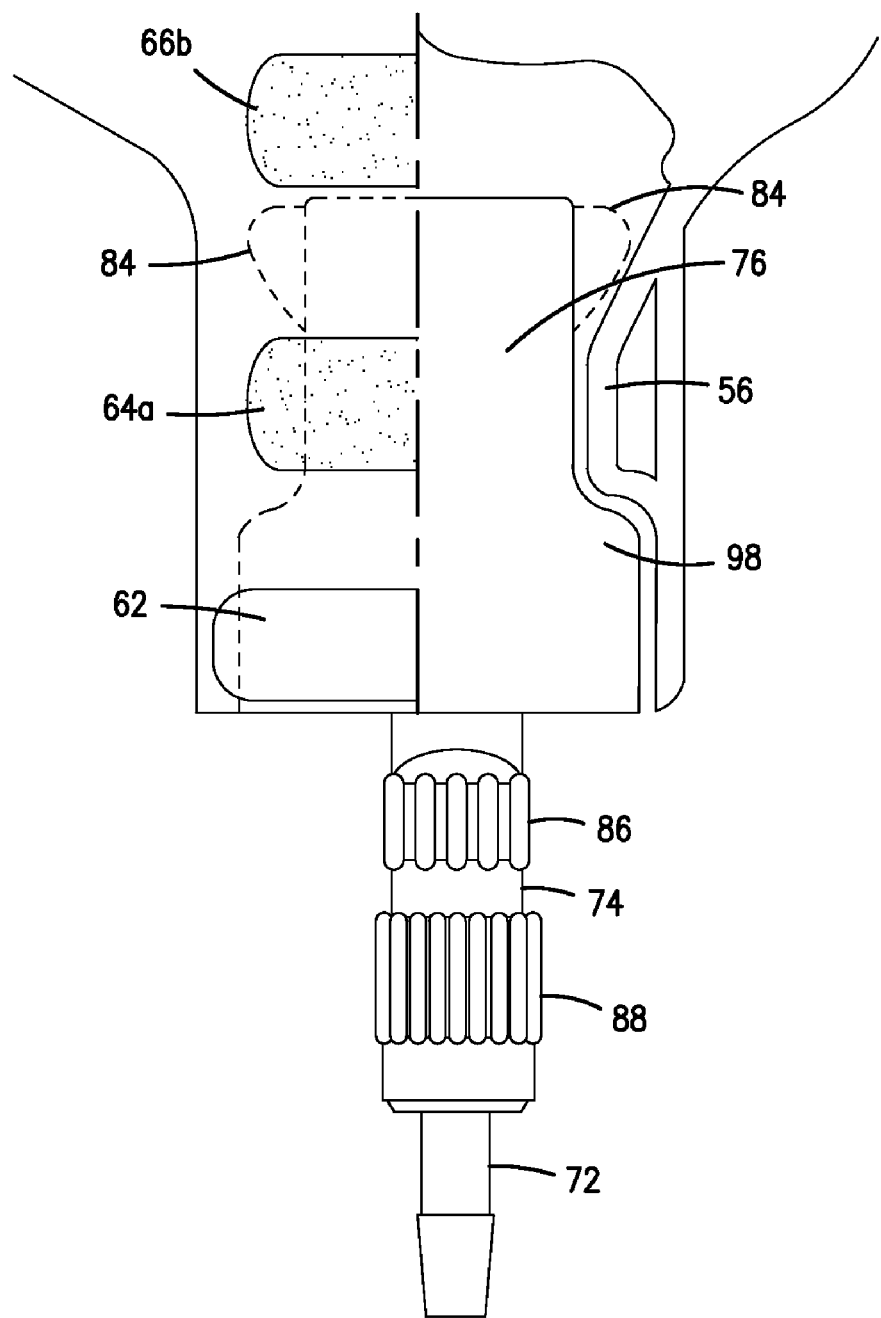
FIG. 11 is a cut away view showing the drainage adapter being coupled to a pouch.

The outer cover 76 is profiled with a shoulder 98 dimensioned to fit within the discharge opening 54 of the pouch 10. Referring to FIG. 11, the shoulder 98 is dimensioned to be stopped by the constriction 56. In use, a wearer attaches the adapter 70a by inserting the adapter 70a into the discharge opening 54 until the shoulder 98 abuts the lower profile 60 of the constriction 56. Thereafter, the wearer grips the finger grippable surfaces of the enlargement actuator 74 and the counter-grip 88 to manipulate the enlargement actuator 74 to expand the end 78a of the outer cover. The expanded end 84 firmly anchors the adapter 70a with respect to the constriction 56 of the discharge portion 30. The expanded end 84 also provides a liquid-tight seal between the adapter 70a and the discharge portion 30 to prevent liquid from leaking between the pouch wall material and the adapter 70a.

The shoulder 98 permits a user to reliably insert and locate the adapter 70a at the correct position within the discharge portion 30 of the pouch. The wearer can feel when the adapter 70a is correctly located abutting the constriction 56, even if the wearer may not be able to see inside the pouch. Moreover, the shoulder 98 ensures that the adapter 70a is located correctly such that, when the end 78a is enlarged (at 84), the enlargement is at the correct position relative to the constriction 56 to form a liquid-tight seal. The positioning of the finger grippable surfaces of the enlargement actuator 74 and the counter-grip 88 below the shoulder 98 ensures that these parts are easily accessible to the wearer, even when the adapter is inserted within the discharge opening 54 of the pouch 10.

Figure 12:
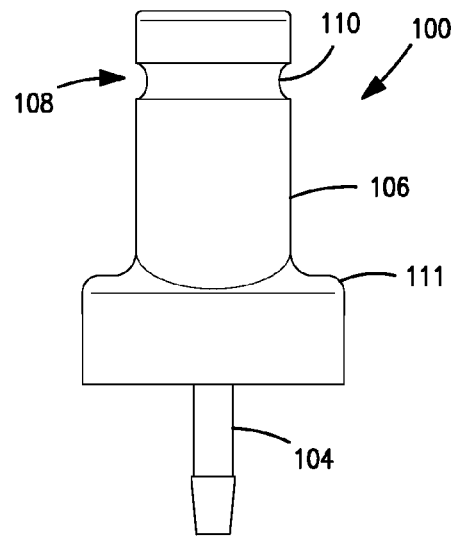
FIG. 12 is a side view of plug of a second example of drainage adapter.
Figure 13:
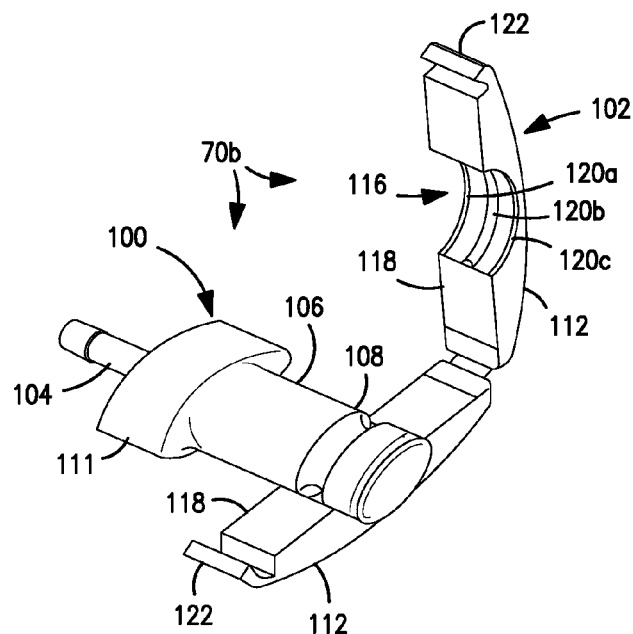
FIG. 13 is a perspective view of the second drainage adapter showing the plug of FIG. 12 in combination with a clamp.
Figure 14:
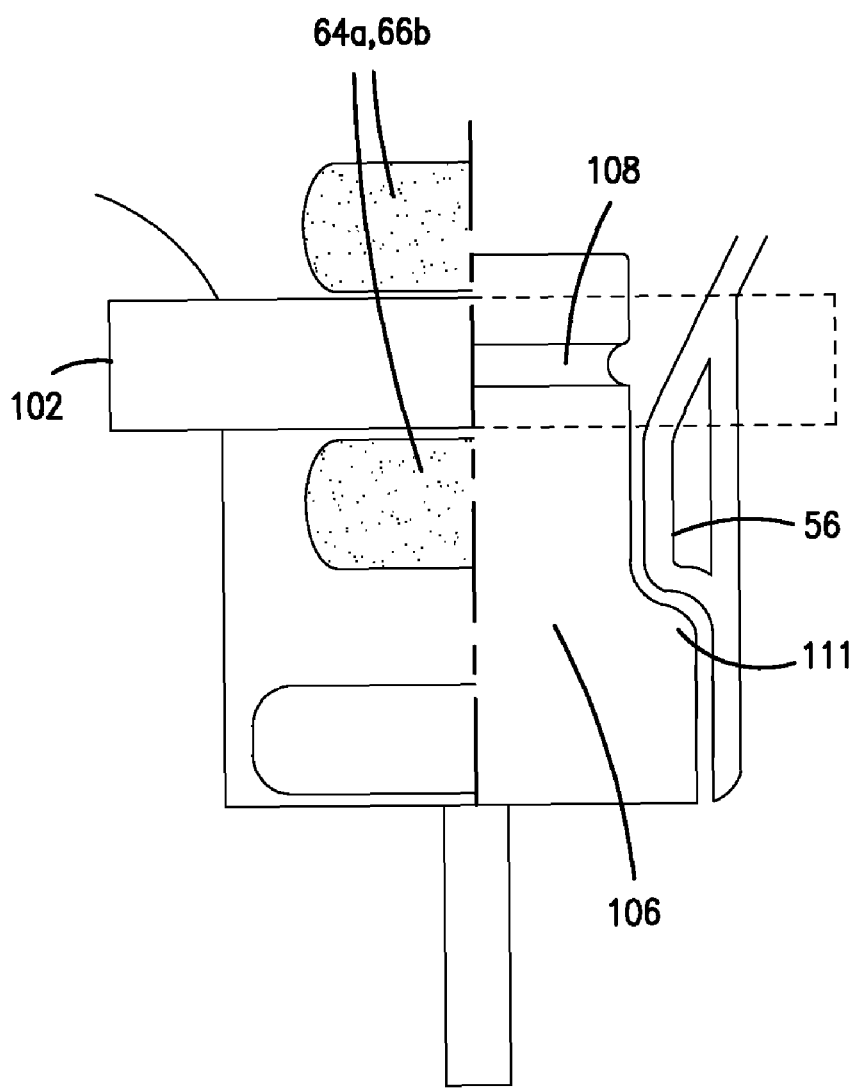
FIG. 14 is a partly cut away view showing use of the second drainage adapter with a pouch.

FIGS. 12 to 14 illustrate a second embodiment of adapter 70b. The adapter 70b comprises two separate or separable parts, including a plug 100 and a clamp 102. In FIG. 13, the plug 100 and the clamp 102 are shown together, to illustrate their mutually shaped portions.

The plug 100 is shaped similarly to the central tube 72 and cover 76 of the adapter 70a described above. The plug includes a central tube 104, and an outer cover 106, integrally molded. The outer cover 106 includes a sealing channel 108. The sealing channel is lined with a channel gasket 110, for example, of an elastomeric material. The gasket may be integrally molded with the outer cover 106, or it may be fitted as a separate item. The outer cover may also include a locating shoulder 111, similar to the shoulder 98 of the adapter 70a.

The clamp 102 comprises first and second limbs 112 joined at one end by a hinge 114, for example, an integrally molded living hinge. Each limb 112 includes a cut-out or recess 116 for fitting around the outer cover 100. Each limb 112 carries a limb gasket 118, for example, of elastomeric material, for sealing against the surface of the pouch. The gasket 118 may be integrally molded with each limb 112, or it may be a separate item attached to the limb 112. Each limb 112 and/or its gasket 118 includes one or more projecting sealing ribs 120. The ribs 120 include a central rib 120b dimensioned to fit within the channel 108 of the plug 100 when the clamp 102 is fitted around the plug. The ribs 120 may include one or more peripheral ribs 120a and 120c for additional local sealing. The central rib 120b may be part of the peripheral ribs 120a and 120c.

The limbs 112 further comprise a clasp 122 formed by interlockable formations at the ends of the limbs 112 opposite the hinge 114. The clasp 122 releasably secure the limbs 112 together in a clamping position.

In use, the wearer firstly inserts the plug 100 into the discharge outlet 54 of the pouch, until the locating shoulder 111 abuts the constriction 56 in the discharge portion 30 of the pouch. Thereafter, the wearer places the clamp 102 on the exterior of the discharge portion 30, such that one of the limbs 112 lies in a predetermined position. For example, the predetermined position may be between two of the distributed mechanical engagement fastener parts 64a and 66b on the rear face 14 of the pouch 10. The limbs 112 are dimensioned to fit relatively snugly between the fastener parts 64a and 66b to make positioning easy. The limbs 112 of the clamp 102 are then closed together around the outside of the discharge portion 30 to clamp the discharge portion 30 against the plug 100, and thereby form a secure liquid-tight seal. The limbs 112 are locked closed by the clasp 122.

In a similar manner to the adapter 70a, the shoulder 111 of the plug 100 enables the plug 100 to be properly located inside the discharge opening 54 of the pouch 10 for engagement by the clamp 102. The wearer can feel when the plug 100 has been fully inserted by the shoulder 111 abutting the constriction 56 inside the discharge portion 30, thereby avoiding any need for the wearer to be able to see inside the discharge portion. The fastener parts 64a and 66b provide highly effective visual and tactile guides for placing the clamp 102 in the correct position on the exterior of the pouch 10, enabling the adapter 70b to be fitted quickly and easily by almost any ostomate.

The sealing gaskets 110 and 118 enable a relatively high sealing force to be applied without significant risk of damaging the pouch wall material. The positive engagement between the sealing channel 108 and the rib 120b provides a highly effective liquid-tight seal.

The plug 100 and the clamp 102 have a generally oval or eye (or almond) shape, to match the natural opening shape of the discharge portion, in order to achieve an optimum liquid-tight seal.

Figure 15:
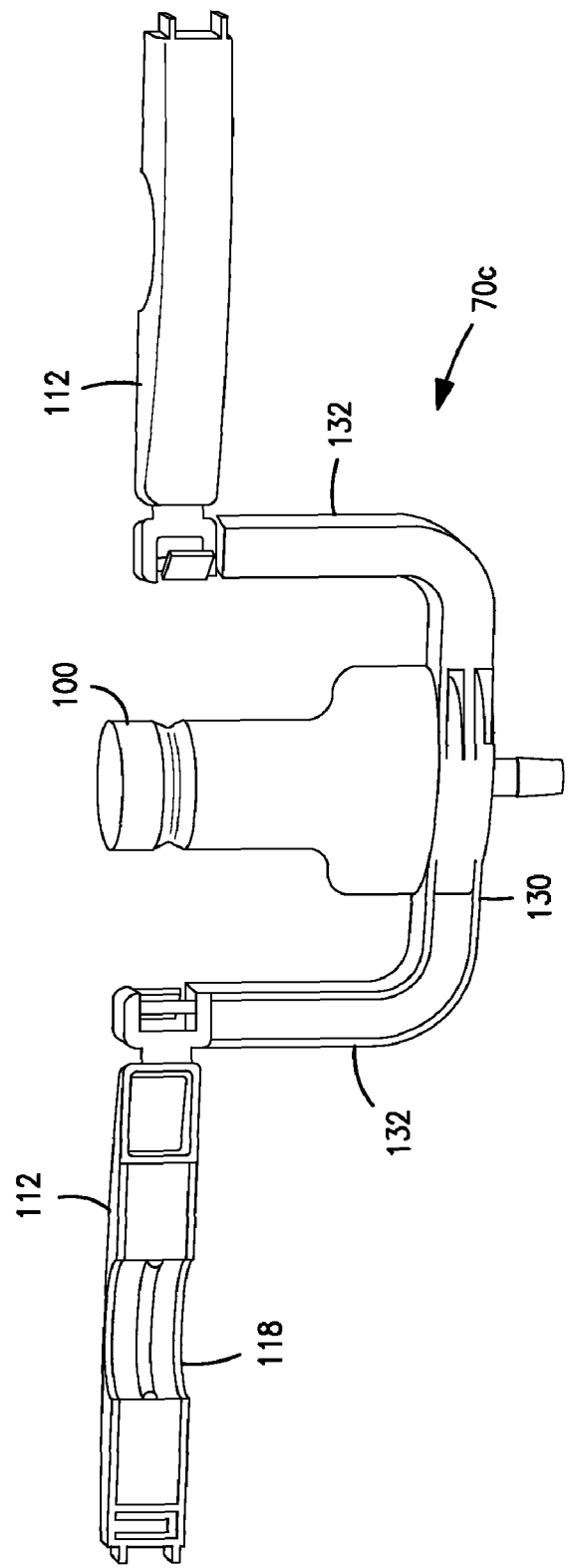
FIG. 15 is a perspective view of a third example of drainage adapter in an open condition.
Figure 16:
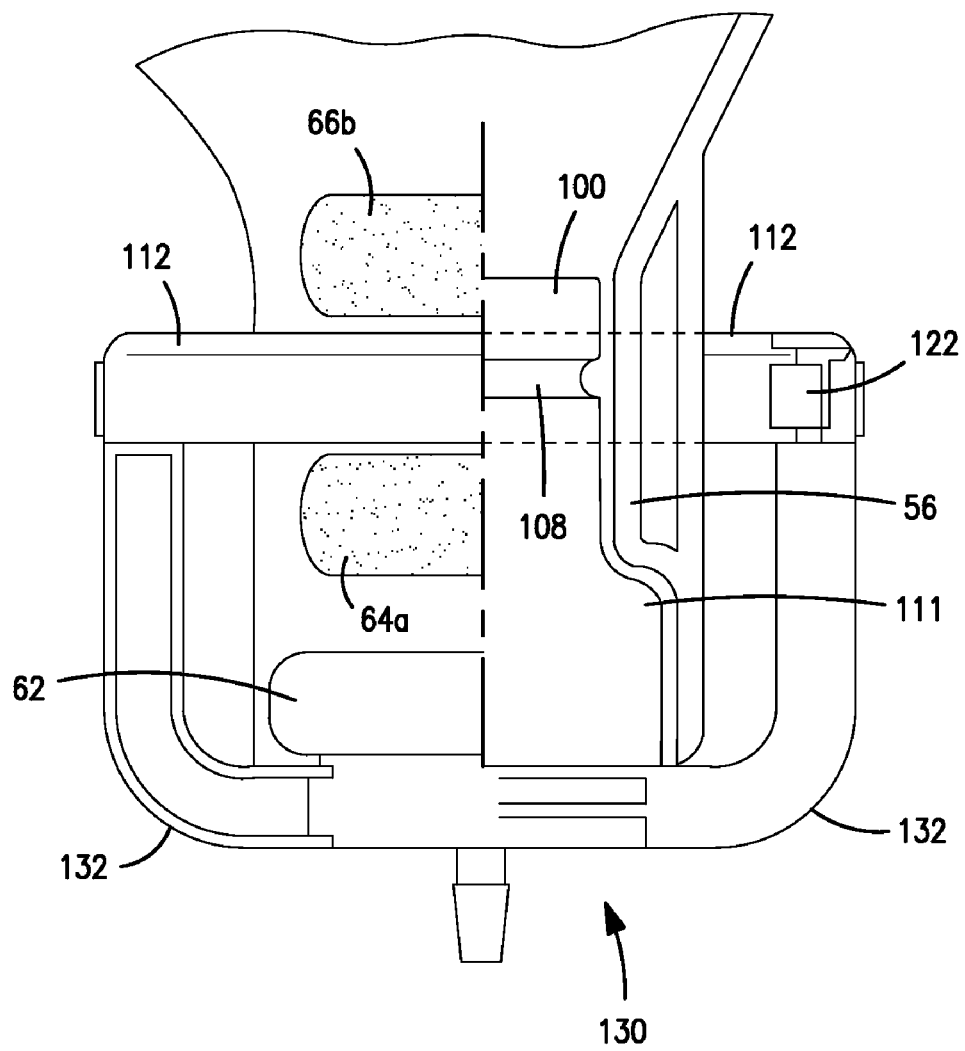
FIG. 16 is a partly cut away view showing the third drainage adapter with a pouch.

FIGS. 15 and 16 illustrate a third example adapter 70c. The third adapter 70c is very similar to the second adapter 70b described above, and the same reference numerals are used where appropriate to denote features already described. The third adapter 70c unifies the plug 100 and clamp portions of the second adapter 70c in a unitary member 130. The member 130 includes supports 132 extending laterally from the plug 100 for carrying the limbs 112 of the clamp. Each support is substantially L-shaped, although other shapes may be used as desired. Each limb 112 is hinged to the respective support 132, for example, by a living hinge.

Compared to the second adapter 70b, the third adapter 70c is a one-piece item (or an assembly of permanently connected parts). Using a one-piece item or assembly reduces the risk of the user accidentally losing either the plug or clamp if these items have to be stored as separate items when not in use. The supports 132 also ensure that the limbs 112 of the clamp are always correctly aligned with respect to the plug 100, thus even further alleviating a burden on the user to correctly locate the clamp in use (on the exterior of the pouch) with respect to the plug (on the inside of the pouch).

Figure 17:
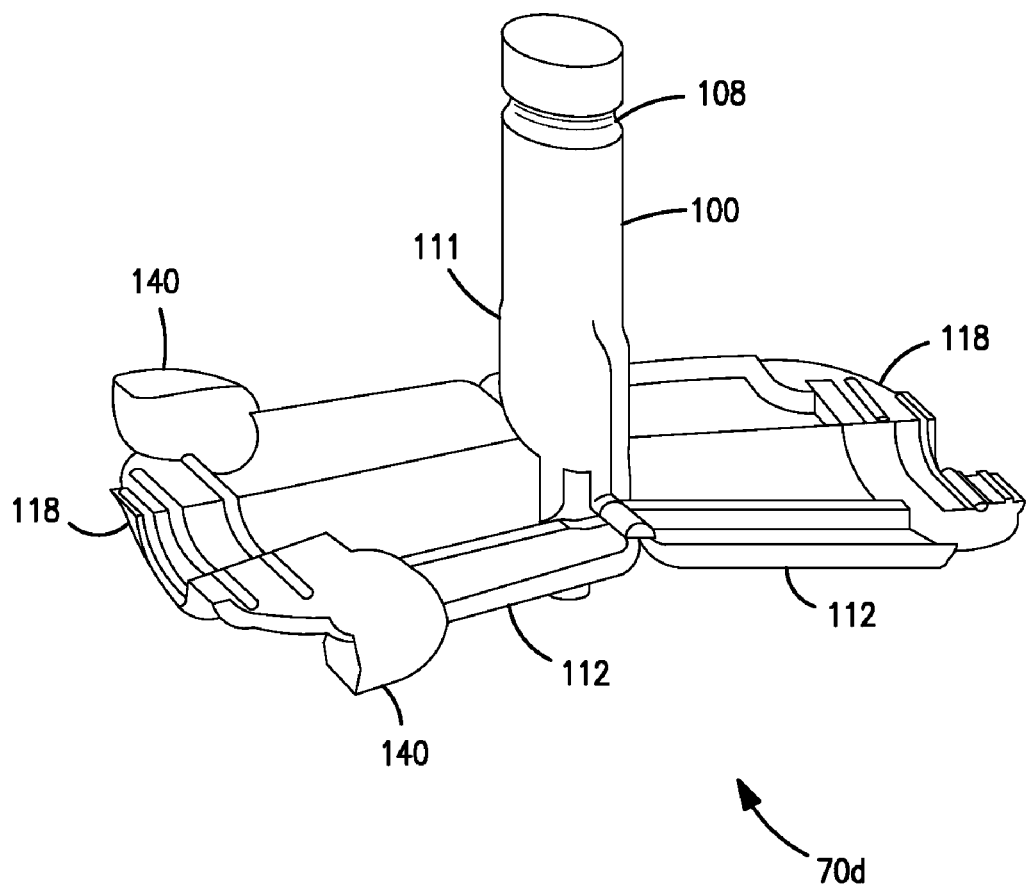
FIG. 17 is a perspective view of a fourth example of drainage adapter in an open condition.
Figure 18:
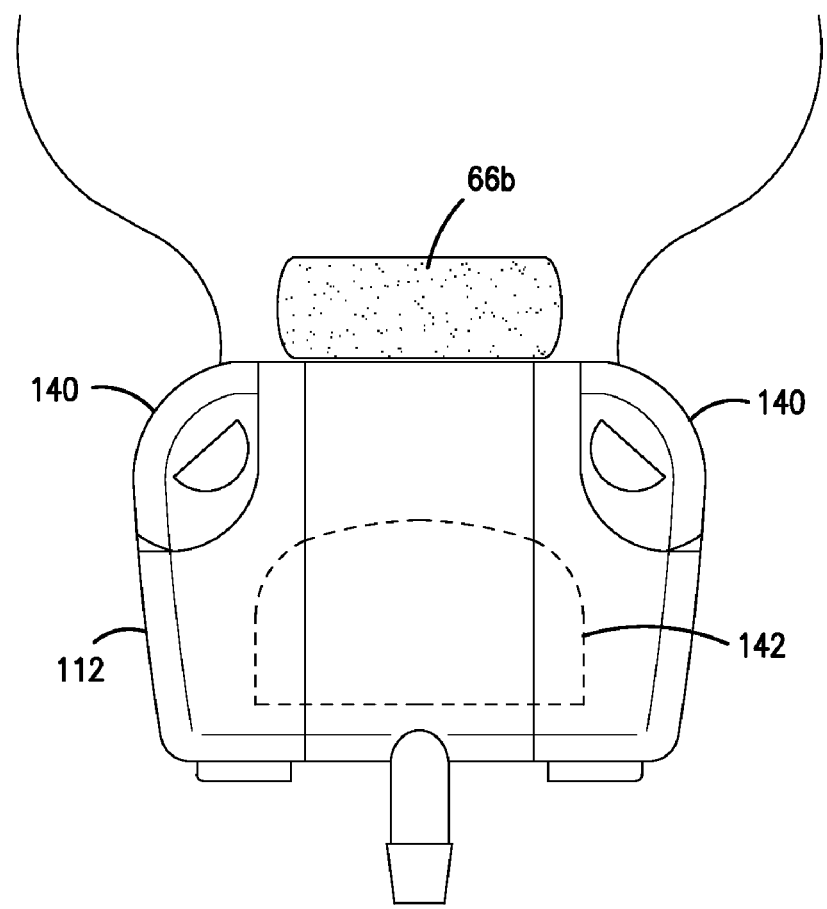
FIG. 18 is a side view showing the fourth drainage adapter in use on pouch.

FIGS. 17 and 18 illustrate a fourth example of adapter 70d. The fourth adapter 70d is similar to the third adapter 70c described above, and the same reference numerals are used where appropriate to indicate features already described. In the fourth adapter 70d, the clamping limbs 112 are hinged to the plug 100 to open and close as a clamshell. Each limb 112 comprises a profiled plate or shell carrying a sealing gasket 118. The limbs 112 are securable together by means of movable tabs or wings 140. The tabs 140 are hinged to either of the limbs 112 to move generally in the same plane as the limb. As indicated in phantom at 142 in FIG. 18, one or both of the shells include a hollow or window, to reduce the amount of plastics material, and hence reduce the cost of manufacture. The hollow allows the user to at least partly view the discharge portion 30 of the pouch 10 even when the adapter 70d is fitted.

It will be appreciated that the adapters 70a-d are configured to interact with the constriction 56 of the discharge portion 30, to facilitate easy insertion of a portion of the adapter into the correct sealing position, without requiring the user to be able to see inside the discharge portion.

The foregoing description is merely illustrative of preferred embodiments of the invention. Many improvements, modifications and equivalents may be used within the scope and/or spirit of the invention.

We claim:

1. A drainable pouch for collecting human body waste, comprising:
   a. first and second walls defining a collection region and a discharge portion with a discharge outlet depending from the collection region, the discharge portion being defined by integral portions of the first and second walls and the discharge portion being foldable to a closed position in which the discharge portion is sealed closed;
   b. wherein the discharge portion comprises a drain passage having a constricted region defined by portions of side seals of the discharge portion, and a widened portion, said widened portion of the drain passage being downstream of the constricted region and having an internal width wider than the internal width in the constricted region;
   c. said discharge portion having two abutment regions within said drainage passage, said abutment regions being adapted to abut against a drainage adapter inserted into said drain passage and facilitate sealing of the adapter within said drainage passage, said two abutment regions defining where said constricted region transitions to said widened portions, and;
   d. two opposing bias members disposed at said discharge outlet, said bias members being squeezable to open said discharge outlet and permit insertion of the adapter into said drainage passage.

2. The drainable pouch according to claim 1, wherein the constricted region has a gradually tapered upper portion.

3. The drainable pouch according to claim 1, wherein the constricted region has a generally abrupt profile in its lower portion.

4. The drainable pouch according to claim 1, wherein a minimum internal width of the constricted region of the drain passage is greater than about 60% of the external width of the discharge portion.

5. The drainable pouch according to claim 1, wherein a minimum internal width of the constricted region of the drain passage is less than about 80% of an internal width of the discharge portion downstream of the constricted region.

6. The drainable pouch according to claim 1, further comprising a baffle upstream of the constricted region of the drain passage.

7. The drainable pouch according to claim 1, wherein said bias members are dimensioned and positioned so that they do not overlap the constricted region of the drain passage when the discharge portion is unfolded from its closed position to a drainable position.

8. The drainable pouch according to claim 1, wherein the pouch is a liquid collection pouch.

9. The drainable pouch according to claim 1, wherein the pouch is an ostomy pouch.

* * * * *